US00PP11611P

United States Patent [19]

Olesen et al.

[11] Patent Number: Plant 11,611

[45] Date of Patent: Oct. 31, 2000

[54] COMPACT FLORIBUNDA ROSE PLANT NAMED 'POULDACE'

[75] Inventors: L. Pernille Olesen; Mogens N. Olesen, both of Fredensborg, Denmark

[73] Assignee: Poulsen Roser ApS, Fredensborg, Denmark

[21] Appl. No.: 09/165,408

[22] Filed: Oct. 2, 1998

[51] Int. Cl.[7] ..... A01H 5/00

[52] U.S. Cl. ..... Plt./145

[58] Field of Search ..... Plt./145, 125

[56] References Cited

PUBLICATIONS

Haring, et al., 1986, Modern Roses 9, The American Rose Society, Shreveport, Louisiana, pp. 102–103.

*Primary Examiner*—Howard J. Locker

[57] ABSTRACT

A new compact floribunda rose plant which has abundant yellow flowers and attrative foliage. The variety successfully propagates from softwood cuttings and is suitable for production in commercial glasshouses and nurseries. This new and distinct variety has shown to be uniform and stable in the resulting generations from asexual propagation.

1 Drawing Sheet

SUMMARY OF THE INVENTION

The present invention constitutes a new and distinct variety of floribunda rose plant which originated from a controlled crossing between Fragrant Delight and an unnamed seedling. The two parents were crossed and the resulting seeds were planted in a controlled environment. The new variety is named 'POULdace'.

The new rose may be distinguished from its seed parent, Fragrant Delight, by the following combination of characteristics:

1. Fragrant Delight has a strong fragrance and 'POULdace' has a light fragrance.

2. The flowers of Fragrant Delight are salmon-orange, while the flowers of 'POULdace' are yellow.

3. Fragrant Delight is a floribunda rose, and 'POULdace' is a compact floribunda rose.

4. The parents of Fragrant Delight are Channelle and Whisky Mac.

The new variety may be distinguished from its pollen parent, an unnamed seedling created by the same inventors, by the following combination of characteristics:

1. The unnamed seedling has a strongr fragrance than 'POULdace'.

2. The unnamed seedling has lower, more compact growth as compared to 'POULdace'.

The objective of the hybridization of this rose variety for commercial greenhouse culture was to create a new and distinct variety with unique qualities, such as:

1. Uniform and abundant flowers;

2. Vigorous and compact growth;

3. Year-round flowering under glasshose conditions;

4. Suitability for production from softwood cuttings in pots.

5. Durable flowers and foliage which make a variety suitable for distribution in the floral industry.

This combination of qualities is not present in previously available commercial cultivars of this type and distinguish 'POULdace' from all other varieties of which we are aware.

As part of their rose developent program, L. Pernille Olesen and Mogens N. Olesen germinated the seds from the aformentioned hybridization and conducted evaluations on the resulting sedlings in a controlled environment in Fredensborg, Denmark.

'POULdace' was selected by the inventors as a single plant from the progeny of the hybridization in May, 1992.

Asexual reproduction of 'POULdace' by cuttings and traditional budding was first done by L. Pernille and Mogens N. Olesen in their nursery in Fredensborg, Denmark in March, 1993. This initial and other subsequent propagations conducted in controlled environments have demonstrated that the characteristics of 'POULdace' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULdace'. Specifically illustrated in SHEET 1:

1. Stem showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULdace', as observed in its growth in glasshouses in Fredensborg, Denmark; Half Moon Bay, Calif., and in a field nursery in Applegate, Jackson County, Oreg. Color references are made using The Royal Horticultural Society (London, England) Colour Chart. 1995, except where common terms of color are used.

For a comparison, serveral physical characteristics of the rose variety 'POULsun', a patented rose variety from the same inventors described and illustrated in U.S. Plant Pat. No. 9,716 and issued on Dec. 3, 1996 are compared to 'POULdace' in Chart 1.

CHART 1

| | 'POULdace' | 'POULsun' |
|---|---|---|
| Petal count | 15–20 large petals | 30–35 petals |
| After open, petal color, upper surface | Yellow Group 9B | Yellow Group 13A |

CHART 1-continued

| | 'POULdace' | 'POULsun' |
|---|---|---|
| After open, petal color, reverse surface | Yellow Group 9C | Yellow Group 13B |

Parents: Fragrant Delight×Unnamed seedling.
Classification:
*Botanical.*—*Rosa hybrida*.
*Commerical.*—Compact floribunda.

FLOWER AND FLOWER BUD

Blooming habit: Recurrent.
Flower bud:
*Size.*—Upon opening, 18 mm–24 mm in length from base of receptacle to end of bud.
*Bud form.*—Blunt to ovoid.
*Bud color.*—As sepals unfold and at ¼ opening, Yellow Group 9A.
*Sepals.*—Green Group 138B–139C. Weak to moderate foliaceous appendages on three of the five sepals. Surfaces of sepals slightly pubescent. Stipitate glands present on outer surfaces of sepals.
*Receptacle.*—Surface: Smooth, glabrous. Shape: Broadly unr-shaped. Size: Small. 5 mm (h) × 6 mm (w). Color: Green Group 138A.
*Peduncle.*—Surface: With moderate number of stipitate glands. Length: 24–40 mm average length. Color: Green Group 138B. On plants grown under high light conditions, penduncles may exhibit intonations of Greyed-Red Group 184A.
*Borne.*—Singly and in small clusters.
Flower bloom:
*Fragrance.*—Light citrus fragrance.
*Duration.*—As a pot plant, flowers last from 6 to 8 days. As a cut flower 4 to 6 days.
*Size.*—Average flower diameter is 55–60 mm when open.
*Form.*—Shape of flower when viewed from the side: Upon opening, upper part: Convex. Upon opening, lower part: Flattened convex. Open flower, upper part: Flattened convex. Open flower, lower part: Concave.
*Petalage.*—Semi-double. Average range: 15–20 large petals under normal conditions. Petals average 26 mm in length and 23 mm in width.
Color:
*Upon opening, petals.*—Upper Surface: Yellow Group 9A. Reverse Side: Yellow Group 9B.
*Upon opening, basal petal spots.*—Outer Side: Yellow Group 9B. Inner Side: Yellow Group 9B.
*After opening, petals.*—Upper Surface: Yellow Group 9B. Reverse Side: Yellow Group 9C.
*After opening, basal petal spots.*—Outer Side: Yellow Group 9B. Inner Side: Yellow Group 9B.
General tonality: On open flower Yellow Group 9A. No change in the general tonality at the end of the second day. After three days, general tonality changes towards Yellow Group 6C–6D.
Petals:
*Petal reflex.*—Petals reflex backwards slightly.
*Petal edge.*—Uniform.
*Shape.*—Round.
*Petaloids.*—Commonly none.
*Thickness.*—Average.
*Arrangement.*—Informal.
*Petal persistence.*—Petals drop off cleanly.
Reproduction organs:
*Pollen.*—Color: As flower opens, pollen colors changes from Yellow Group 13B to Greyed-Orange Group 163A. Abundance: Average.
*Anthers.*—Size: Small. Color: Yellow Group 13B. Abundance: Average.
*Filaments.*—Color: Yellow Group 14B.
*Stigmas.*—Stigmas superior in position to anthers. Color: Yellow Group 14B.
*Styles.*—Color: Yellow Group 14B.
*Hips.*—None observed.

PLANT

Plant growth: Vigorous, compact, and bushy. When grown as a 15 cm pot plant, the average height of the plant itself is 20 to 22 cm and the average width is 20 to 24 cm. When grown as a nursery plant (on its own roots) the average plant height is 55–65 cm and the average plant width is 55–60 cm.
Stems:
*Color.*—Young wood: Green Group 143B. Older wood: Green Group 138B.
*Thorns.*—Incidence: Moderate, with numerous small prickles. Size: Average length: 3 mm–4 mm. Color: Yellow-Green Group 145D with slight intonation on some thorns of Red Group 49D. Shape: Linear.
*Surface.*—Young wood: Smooth. Older wood: Smooth.
Plant Foliage: Normal number of leaflets on normal leaves in middle of the stem: 5 leaflets.
*Leaf size.*—Small to medium. 90 mm (l)×60 mm (w).
*Abundance.*—Average.
*Color.*—Upper Leaf Surface: Green Group 137A–143B. Lower Leaf Surface: Green Group 138B. Juvenile Foliage: Green Group 143A. Anthocyanin intonation: Limited. Location: Margins of leaflets. Color: Greyed-Red Group 179A.
Plant leaves and leaflets:
*Stipules.*—Size: Average 10 mm length. Color: Green Group 137B. Presence of stipitate glands: Present on distal ends.
*Petiole.*—Length: 20 mm–22 mm. Color: Green Group 137B. Underneath: Prickles presnet. Margins: Stipitate glands present on margins and underneath.
*Rachis.*—Color: Green Group 137B. Underneath: Prickles present. Margins: Stipitate glands present on margins and underneath.
*Leaflet.*—Edge: Serrated. Shape: Ovate.
*Other.*—Moderately glossy finish. Thin texture.
Disease resistance: Average resistance to black spot under normal growing conditions in Half Moon Bay, Calif.; Jackson County, Oreg., and Fredensborg, Denmark.
We claim:
1. A new and distinct variety of rose plant of the compact floribunda class, substantially as herein illustrated and described as a distince and novel rose variety due to its abundant, yellow flowers, vigorous and compact growth, suitability for production from softwood cuttings and traditional budding in commercial glasshouses and nurseries, and durable flowers and foliage which make the variety suitable for distribution in the floral industry.

* * * * *

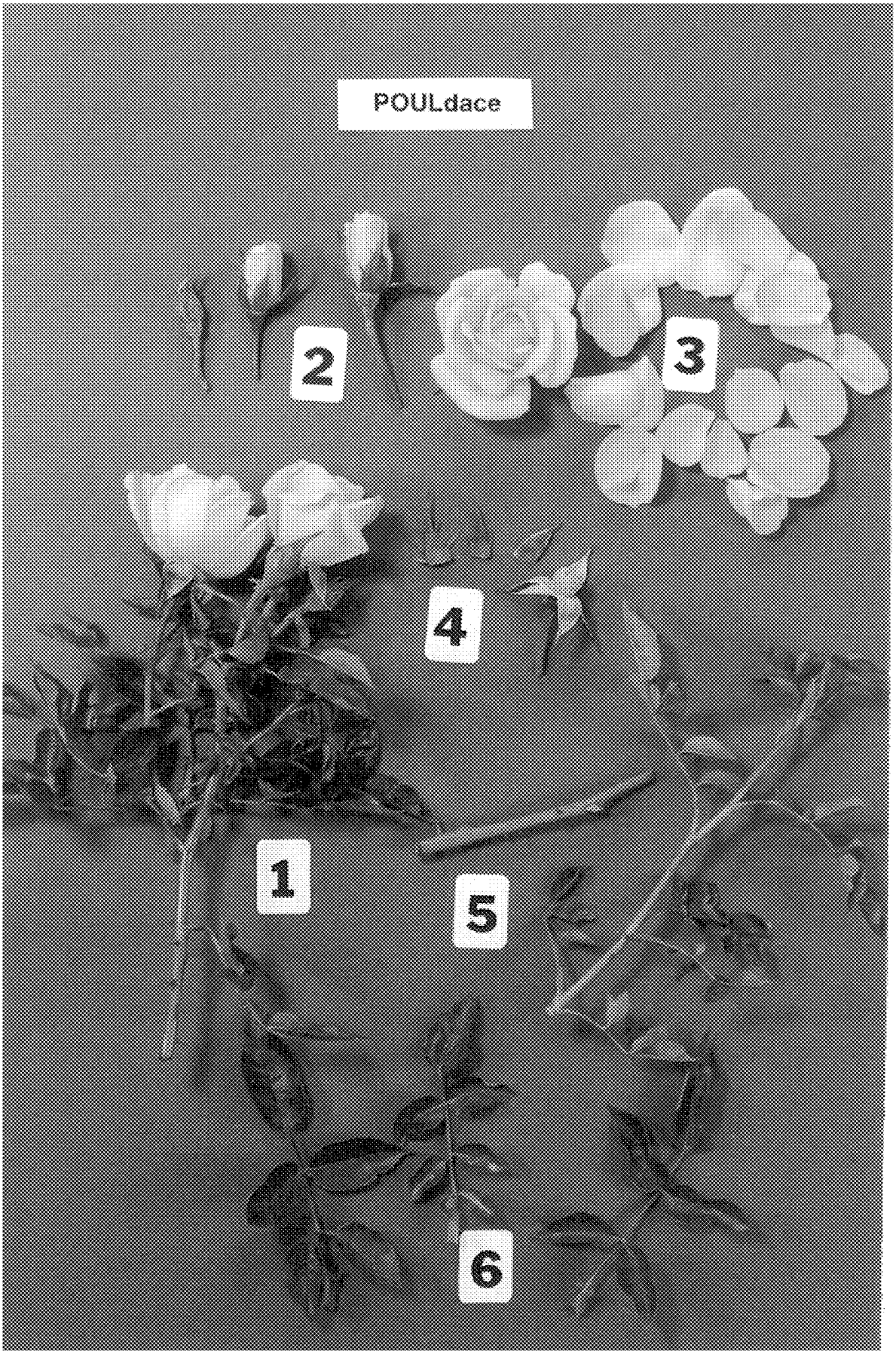
POULdace
2
3
4
1
5
6